United States Patent [19]

Oksman et al.

[11] Patent Number: 5,250,160

[45] Date of Patent: Oct. 5, 1993

[54] APPARATUS AND METHOD FOR DISINFECTING A CONTAMINATED OBJECT

[76] Inventors: Henry C. Oksman, 20 Wagon Wheel Rd., Mamaroneck, N.Y. 10543; Joseph Eisner, 185 E. 85th St., New York, N.Y. 10028

[21] Appl. No.: 843,745

[22] Filed: Feb. 28, 1992

Related U.S. Application Data

[63] Continuation-in-part of Ser. No. 532,624, Jun. 4, 1990, Pat. No. 5,118,401.

[51] Int. Cl.$^5$ .............................. C25F 5/00; C25B 1/26; C25B 9/00
[52] U.S. Cl. ...................................... 204/131; 204/228
[58] Field of Search ................ 204/130, 242, 131, 228

[56] References Cited

U.S. PATENT DOCUMENTS

| | | | |
|---|---|---|---|
| 1,902,390 | 3/1933 | Wormley | 204/242 X |
| 2,600,107 | 6/1952 | Gelfand et al. | 204/131 |
| 4,268,367 | 5/1981 | Reis et al. | 204/130 X |
| 4,710,233 | 12/1987 | Hohmann et al. | 204/130 X |
| 5,129,999 | 7/1992 | Holland et al. | 204/242 X |

FOREIGN PATENT DOCUMENTS 2550946  3/1985  France .
2094992  9/1982  United Kingdom .

*Primary Examiner*—Donald R. Valentine
*Attorney, Agent, or Firm*—Fiddler Levine & Mandelbaum

[57] ABSTRACT

A system and method for applying a disinfectant solution which may include a salt and a buffer to an instrument, object or mass wherein the solution is selectively rendered disinfecting and neutral by impressing a voltage across it to ionize an unstable salt which yields toxic ions only while the voltage is applied. The system can be used to disinfect both metallic and plastic instruments.

12 Claims, 5 Drawing Sheets

APPARATUS AND METHOD FOR DISINFECTING A CONTAMINATED OBJECT

This application is a continuation-in-part of U.S. patent application Ser. No. 07/532,624 filed Jun. 4, 1990, now U.S. Pat. No. 5,118,401.

BACKGROUND OF THE INVENTION

There has long been a need for disinfecting medical instruments between applications to the body, particularly in sensitive areas, e.g. the eyes, in order to prevent transmission of disease causing bacteria and viruses. Recent isolation of immunodeficiency virus from tears of patients with AIDS and the isolation of Herpes Simplex virus type one, Hepatitis B virus and Adenovirus has heightened interest in the transmission of these diseases. Herpes Simplex Viral eye disease is a leading cause of corneal blindness in the United States and other industrialized nations, as well as developing countries throughout the world. Herpetic eye disease in the United States occurs in about one half million people per year. Ten million people are estimated to be affected annually worldwide and several million people are visually impaired as a result of Herpetic eye disease. Trachoma, caused by a chlamydial organism is a chronic and progressive infectious disease which is the world's leading cause of preventable blindness. It is a potential contaminant of ocular instruments worldwide.

Bacteria such as Staphylococcus, Pseudomonas, Bacillus, Pneumococci and Acanthamoeba are serious causes of ocular infections. Common fungi such as Fusarium Solani, Aspergillus Fumigatus and Candida Albicans contribute to a large number of fungal infections. All are potential agents for contaminating ocular instruments during routine examinations.

There is increased pathogenic flora in contact lens wearers, thus raising the potential for instrument contamination whenever such patients are being examined. The number of reported cases of Acanthamoeba Keratitis has increased dramatically in recent years. These organisms are known to exhibit a propensity to adhere to the walls of plastic containers, thereby being potential contaminants in ophthalmological settings.

The American Academy of Ophthalmology recommends soaking tonometer heads in a dilute Clorox solution. Alcide Corporation developed a two compound product called Exspor that has to be mixed and then diluted. This chlorous acid based chemical sterilizes within three minutes and disinfects spores only after the disinfected article is soaked in the solution for six hours. Another commonly used disinfectant is three percent hydrogen peroxide. It destroys spores when the disinfected article is soaked for four hours. An alternate agent is seventy percent isopropyl alcohol wipes, recommended for preventing possible transmission of viruses from tears, via tonometers.

Present methods for disinfecting non metallic ocular instruments are cumbersome and time consuming both in preparation and implementation. The chemical solutions used are toxic and in some cases require special precautions in order to prevent any potential risk of chemical residue getting into the eye. For example, fluffy white corneal lesion was seen in a patient immediately after applanation tonometry. The tonometer applanation surface had been disinfected with peroxide solution overnight. Slit-lamp examination revealed a circular corneal epithelial defect corresponding in size to the tonometer applanation surface. In another case, damage to the cornea was a result of wiping the tonometer with seventy percent isopropyl alcohol. After using the applanation tonometer, slit-lamp examination of a thirty-eight year old woman with type I diabetes mellitus revealed a circular area of corneal epithelial opacification corresponding to the size of the tonometer applanation surface.

Disinfection systems are needed, not only for medical instruments, but for other objects, metallic and non-metallic, which are used in environments where infectious organisms are concentrated and where such organisms are likely to come into human contact or even be ingested or inspired by humans.

Current disinfection systems use chemicals which are toxic to the environment, heat, ultra-violet light, X-rays and other radiation which can be physically damaging. What is needed is a disinfection system which employs a disinfection agent that is normally benign but can be selectively rendered active for attacking and killing infectious organisms.

SUMMARY OF THE INVENTION

The present invention overcomes the aforementioned disadvantages of the prior art by teaching the construction of a system for applying a disinfectant to an instrument or other object or group of objects or a mass of matter inhabited by infectious organisms. More specifically, the present invention teaches the construction of an electrochemical disinfection system for sterilizing an instrument comprising container means for receiving said instrument while it is being disinfected, a solution contained within said container means for enveloping said instrument while it is received in said container means, two electrodes disposed in contact with said solution, a voltage source connected between said electrodes for applying a voltage thereacross, said solution being conductive for conducting an electric current between said electrodes during application of said voltage, said current generating ions in said solution for dispersion into contact with said instrument for disinfecting said instrument, wherein said conductive electrolytic salt is selected from the group consisting of NaCl, $Na_2SO_4$, $CaSO_4$, NaI and KBr and further comprising a phosphate buffer selected from the group consisting of $NaH_2PO_4$, $Na_2HPO_4$ and $Na_3PO_4$.

It is therefore an object of the invention to provide a system for disinfection of an object or mass which can be selectively activated and deactivated.

Another object of the invention is to provide a system for disinfection of an object or mass which is benign when deactivated but which is rendered destructive to infectious organisms when activated.

Still another object of the invention is to provide a system for disinfection of an object or mass having a disinfection period limited to several minutes.

Still a further object of the invention is to provide a system for disinfection of an object or mass in which current flow is used to render a solution disinfecting to objects and masses irrespective of whether or not they are within the path of the current flow.

Other and further objects of the invention will be apparent from the following drawings and description of a preferred embodiment of the invention in which like reference numerals are used to indicate like parts in the various views.

DESCRIPTION OF THE PREFERRED EMBODIMENTS

Figures 1, 2, 3:
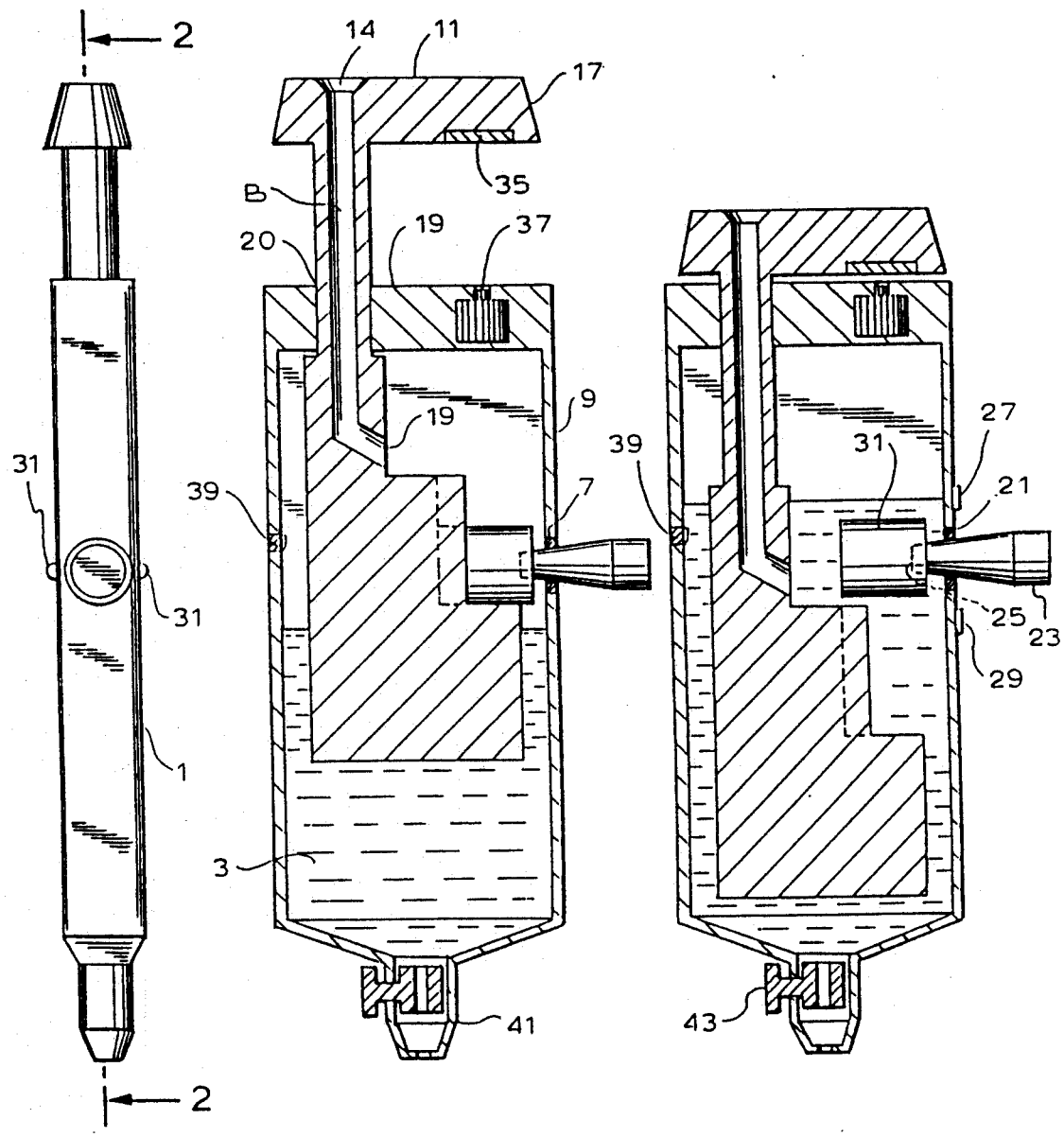
FIG. 1 is a front elevation view of the apparatus of the preferred embodiment of the invention.
FIG. 2 is a side sectional elevation view of a first preferred embodiment of the invention in a first disposition.
FIG. 3 is a side sectional elevation view of the first preferred embodiment of the invention in a second disposition.

The first preferred embodiment of the invention utilizes a device including an electrolytic cell where current flows for a designated period of time, preferably one to five minutes. A tonometer applanation surface is inserted into the device and disinfected within a short period, leaving no toxic residues or chemicals on the applanation surface.

Aqueous sodium chloride (normal saline) with three percent hydrogen peroxide is a commonly used disinfectant. When this solution is used in an electrolytic cell, reduction reactions at the cathode deliver free electrons. This results in the formation of very reactive free radicals that increase the disinfection potential of the solution.

Although generation of free radicals, specifically superoxides, is increased by the presence of hydrogen peroxide in an electrolytic solution, peroxide is not essential, as superoxide will form in the electrolysis of normal saline without peroxide. During the electrolysis of a purely saline solution, with or without peroxide, chlorine gas escapes, sodium hydroxide concentration increases and pH rises. For disinfecting an instrument intended to contact the eye, it is important for additional nonelectrolyzable solutes to be added to the solution and the amount of saline reduced. The relative proportion of solutes determines the concentration of free radicals and other ions generated under given voltage-current conditions. Two of the acceptable non electrolyzable solutes are NaI or $Na_2SO_4$.

The power (P) delivered to an electrolytic cell is the product of the applied voltage (V) multiplied by the current (I) passing between the electrodes:

$$P = V \cdot I$$

Current is dependent on the concentration of conductive electrolytic ions in solution, the distance between electrodes (d) and the applied voltage (V). Another important factor is the ionization potential. As the voltage to the cell is increased the strength of the electric field (E) generated is increased according to $$E = V/d$$

Ionization potential is directly proportional to electric field strength. As the applied voltage is increased additional species of solution constituents ionize. Ion concentration can, hence, be controlled by varying the applied voltage. When hydrogen peroxide is present, a greater number of superoxide ions are generated. As used herein "ionization" of salts refers to the breakdown of the salt molecules which frees the constituent elements of the molecules or radicals of them beyond the normal partial disassociation which takes place when salts are dissolved in solution.

If the time required for a ten fold reduction in viability, referred to as the "D Value," is too long more free radicals and other ions are needed. These can be increased either by raising current or voltage input. Increasing power input affects electrode surface current density and its degradation. It also increases the species generated. At very high field values even the stable solutes will electrolyze. Therefore voltage-current values can be changed within a limited range. Another method to add more free radicals is to increase either NaCl concentration, peroxide concentration, or concentration of other electrolyzable salts.

The disinfection system of the invention utilizes common disinfectants such as $Cl_2$, $I_2$, $O_2$, $H_2O_2$, NaOH or other ions as desired. A significant contribution to the disinfection process is the generation of very specific, short lived disinfectant ions or free radicals.

Referring now to FIGS. 1, 2 and 3 of the drawings there is shown a disinfection system for disinfecting the applanation surface of a tonometer. It will be apparent that other instruments may be similarly disinfected.

The disinfection system includes a hollow vessel 1 of rectangular cross section which can be attached to a slit-lamp by a swing arm (not shown). The vessel 1 is partially filled with a disinfectant solution 3 below opening 7 in vessel wall 9. A floatation plunger 11 having a bore 13 with an inlet 14 in a plunger handle portion 17 thereof and an plunger outlet 19 near the top of a stepped portion of the floatation plunger 11 floats freely in the disinfectant solution 3. The vessel 1 has a cover 19 with an aperture 20 congruent to a uniform cross section of an elongated length of the floatation plunger 11.

The disinfectant solution 3 is preferably composed of a solution containing from zero to five percent hydrogen peroxide and conductive electrolytic salts. The salt composition can be chosen from a variety of compounds such as NaCl, $Na_2SO_4$, $CaSO_4$, NaI and KBr. In order to avoid large pH variations a buffer is also desired. Phosphate buffers, e.g., $NaH_2PO_4$, $Na_2HPO_4$ or $Na_3PO_4$ are stable under electrolysis and can be added to limit pH variations. For use with tonometers or any other instrument intended to contact the eye, solution tonicity should be in a range between half to twice isotonic concentration. However, in order to enhance disinfection, the tonicity of the solution is desirably at least ten percent (10%) above or below isotonic concentration. That is, it is desirable that the solution tonicity be in the range from 50% to 90% of isotonic concentration or from 110% to 200% of isotonic concentration. The solute composition necessary to maintain tonicity in this range is a function of the physical layout of the electrolytic cell, electrode sizes, composition of other solution constituents, and the applied voltage or current.

The following solutions have been found suitable for disinfecting tonometers upon application of an ionizing voltage.

| Solution No. 1 | |
|---|---|
| Sodium Phosphate ($Na_3PO_4$) | 9.2565 grams/liter |
| Sodium Chloride (NaCl) | 0.8951 grams/liter |
| Sodium Iodide | 2.2950 grams/liter |
| Solution No. 2 | |
| Sodium Sulphate ($Na_2SO_4$) | 14.484 grams/liter |
| Sodium Chloride (NaCl) | 1.7902 grams/liter |
| Sodium Iodide (NaI) | 4.5900 grams/liter |

Although the above solutions have been found optimal, approximations to the concentrations set forth above will still be effective to achieve disinfection, e.g., when the concentrations are within 15% of the amounts set forth above. The above solutions are preferably subjected to an electrolyzing voltage of 7.6 volts at 200 milliamperes of current alternated 7.5 times per minute (0.125 Hz) to render them disinfecting.

The electrodes can be formed from an alloy of 80% platinum and 20% iridium. Rectangular electrodes that are 24 mm long and 14 mm high have been found suitable when placed 16 mm apart. Circumscribing the opening 7 in the vessel wall 9 is an O-ring seal 21 having an inner circumference equal to the outer circumference of a portion of the frustoconical housing of a tonometer 23 for removably mounting the tonometer 23 in the opening 7 with the tonometer applanation surface 25 disposed within the vessel 1. Also mounted on the vessel wall 9 adjacent the opening 7 and in diametric opposition are a photodiode 27 and a photodetector 29 directed toward one another so that light emitted by the photodiode 27 impinges upon the photodetector 29 except when a tonometer 23 is mounted in the opening 7 of the vessel wall 9, at which time the tonometer 23 obstructs the light path between the photodiode 27 and photodetector 29 so that no detectable light is received by the photodetector 29.

Also mounted on opposite sides of the vessel walls 9 at no less than the same elevation as the opening 7 in the wall 9 are cell electrodes 31 between which a current can be conducted through the disinfectant solution 3. The cell electrodes 31 should have poorly oxidizing properties, yet act as catalysts in the electrolysis of peroxide and other ions. Heavy metals such as palladium, rhodium, platinum and the like have excellent properties for this purpose.

Disinfectant solution 3 is added to the vessel 1 in a quantity sufficient to rise above the opening 7 in the vessel wall 9 when the floatation plunger 11 is moved downward to the point where a latch ferromagnetic pole piece 35 in the plunger handle 17 engages a latch electromagnet 37 mounted in the vessel cover 19. Fluid level sensor 39 is mounted in the vessel 1 and detects a difference in electrical potential in the solution caused by flow of a leakage current between the electrodes 31 when they are covered with the disinfectant solution 3, i.e., when the level of the disinfectant solution 3 is above the opening 7 in the vessel wall 9, and above the tonometer applanation surface 25 of the tonometer 23 mounted in the opening 7.

The vessel 1 is fitted with a spout 41 on its underside in which there is mounted a normally closed spigot 43 which can be opened to drain the disinfectant solution 3 from the vessel 1.

Figure 5:
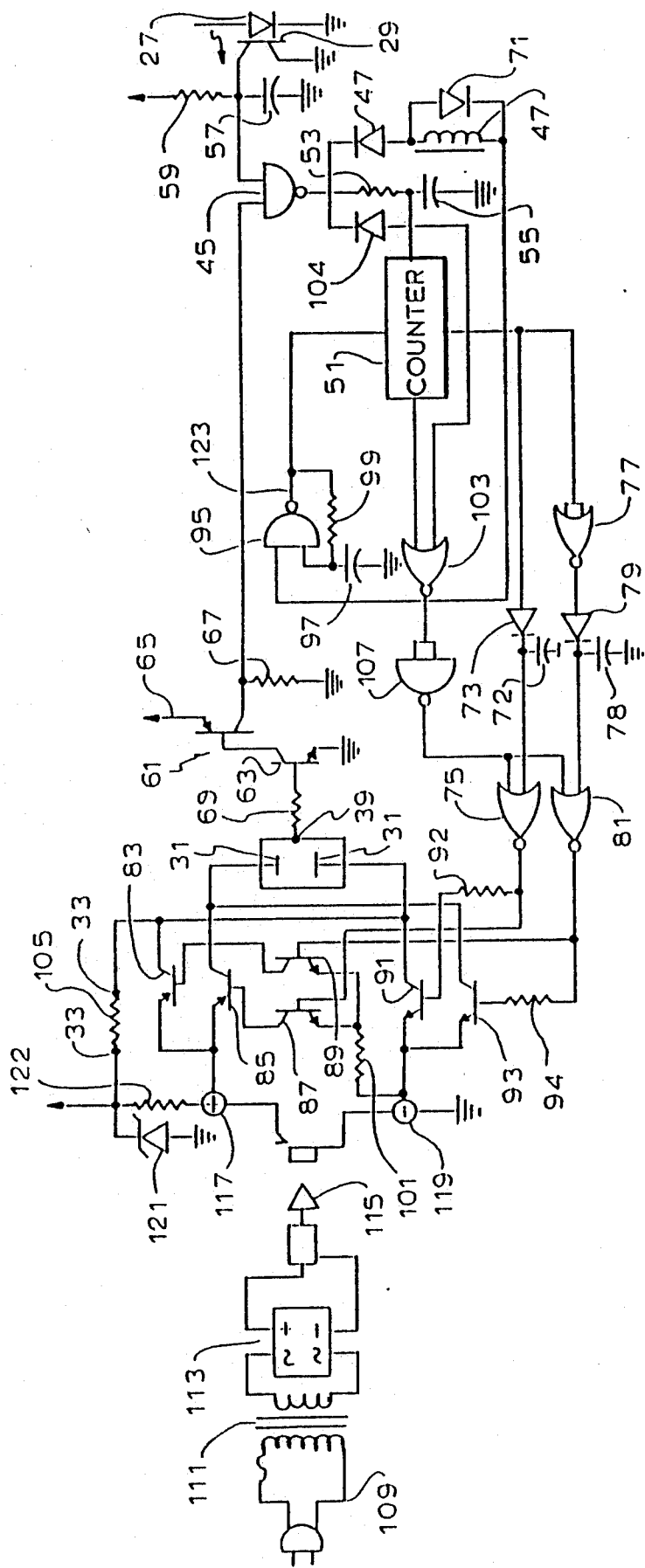
FIG. 5 is a schematic circuit diagram of the first preferred embodiment of the invention.

Referring additionally to FIG. 5 of the drawings wherein the control circuitry 2 is shown, the photodiode 27 directs light across the opening 7 which is sensed by the photodetector 29. The photodetector 29 is connected to one input of a NAND gate 45 which receives a low signal from the photodetector 29 in the absence of a tonometer 23 in the opening 7 of the vessel wall 9. This results in a high signal at the output of the NAND gate 45, which biases a diode 47 to prevent current flow to the inductor 49 of the latch electromagnet 37. The high output of the NAND gate 45 is applied to the reset input of a counter 51 via an RC network including resistor 53 and capacitor 55 to keep it in the reset condition and unable to count. Following a power outage, the system is reset by the RC network composed of capacitor 57 and resistor 59 when electric power is restored by applying a signal to the NAND gate 45.

The other input of the NAND gate 45 is connected to the output of an amplifier 61 which is formed by transistor 63, transistor 65 and resistor 67. Resistor 69 applies a signal from fluid level sensor 39 to the input of amplifier 61 only when the level of the disinfectant solution 3 is above the electrodes 31. When the level of the disinfectant solution 3 is below the electrodes 31, the output signal from the NAND gate 45 is low. This also results in a high signal at the output of the NAND gate 45 which biases the diode 47 to prevent current flow to the inductor 49 of the latch electromagnet 37 and keeps the counter 51 reset and unable to count. A diode 71 in parallel with inductor 49 deenergizes the latch electromagnet 37 at the end of the cycle.

The amplifier 61 formed by transistor 63, transistor 65 and resistor 67 applies a high signal to the other input of NAND gate 45 when the solution 3 is above the tonometer opening 7. When the disinfectant solution 3 is above the opening 7 and the tonometer 23 is mounted in the opening 7, the output of NAND gate 45 goes low, thereby enabling the counter 51 to count and the latch electromagnet 37 to be energized to attract the latch ferromagnetic pole piece 35.

When enabled, counter 51 periodically changes the logical level of its output signal which is conducted through diode 73 to NOR gate 75 at predetermined times, e.g., 8 times during the disinfection cycle, and at the same time, the signal is inverted in inverter 77 and then conducted through diode 79 to nor gate 81. When the output of diode 73 is high, the output of diode 78 is low and vice versa. The capacitor 72 and diode 73, and the capacitor 78 and diode 79 ensure that before the signal goes high at each respective line there will be a delayed low signal. This delay ensures that the current in the chamber will be turned off before it changes polarity. Otherwise an electrical short is possible. Hence, while, the counter 51 is counting, the polarity of the current in the cell reverses resulting in a square wave having a period determined by the selected count output of the counter 51. Transistors 83, 85, 87, 89, 91, and 93 switch the current direction between the cell electrodes 31. The frequency at which the cell electrodes 31 change polarity is determined by the frequency of an oscillator 123 composed of NAND gate 95, capacitor 97 and resistor 99 in conjunction with the counter 51. The oscillator 123 provides high frequency pulses to the clock input of the counter 51.

The sensor amplifier 61 transmits a signal to the electronic circuit regarding solution level status. The presence of the tonometer cylinder is continuously monitored by the photodiode 27 and photodetector 29.

When the output of NOR gate 75 is high it enables transistor 87, transistor 91 and transistor 85 to be turned on for positive square wave current between the cell electrodes 31. When the output of NOR gate 81 is high it enables transistor 89, transistor 93 (through resistor 94), and transistor 83 to be turned on for negative square wave current between the cell electrodes 31. The inverter 77 keeps the square wave current in phase during cycling of the alternating voltage.

When the alternating input voltage is positive, transistor 91 is turned on via resistor 92. At the same time, transistor 87 conducts current from the base of transistor 85 via resistor 101 to ground thereby turning transistor 85 on. At this time transistors 93, 89, and 83 are off thereby causing current to flow through the cell from top electrode to bottom electrode in the orientation of FIG. 5.

When the output of counter 51 is low, transistors 91, 87, and 86 are turned off and, correspondingly, transistors 93, 89, and 83 are turned on thereby causing the current to flow through the cell from bottom electrode to top electrode in the orientation of FIG. 5.

At the end of the cycle, the counter 51 times out and outputs a signal which is conducted to one input of inverter 103, the other input of which is connected to the output of NAND gate 45 through resistor 105. When either the cycle has ended or the tonometer 23 is out of the opening 7, the output of inverter 103 goes low causing output of inverter 107 to go high. This in turn causes the outputs of NOR gate 75 and NOR gate 81 to remain low preventing transistors 87 and 89 from turning on so that no current flows in the cell between the cell electrodes 31. In this way the counter 51 acts as a timed current switch to allow current to flow between the cell electrodes 31 for a predetermined period of time.

A plug 109 connected to a standard wall outlet supplies AC power to a transformer 111 where the voltage is stepped down and then rectified by a rectifier 113. The resulting DC voltage is then applied, via a connector 115, across terminal 117 and terminal 119 where it is regulated by a Zener diode 121 connected to a resistor 122. The transformer 111 and rectifier energize the cell electrodes 31.

A resistor 105 provides a leakage current through the electrodes 31 to enable the fluid level to be detected when it rises to a level submerging the electrodes 31 and the tonometer applanation surface 25.

If the tonometer 23 is out of the vessel wall opening 7, or the level of the disinfectant solution 3 is low, i.e., below electrodes 31, a low signal at the output of NAND gate 45 deenergizes the electromagnet coil 49 and resets the counter 51.

In use, a predetermined quantity of disinfectant solution 3 is poured into the vessel 1 preferably, although not necessarily, through the bore 13 in the plunger 11. The quantity is such as to be below the opening 7 in the wall 9 when the plunger 11 is upwardly disposed or entirely out of the vessel 1 and to rise above the opening 7 when the plunger 11 is fully inserted into the vessel 1. Before full insertion of the plunger 11, a tonometer 23 is mounted in the opening 7 of the vessel wall 9.

The operator then presses the plunger handle 17 to push the floatation plunger 11 into the disinfectant solution 3, thereby causing the fluid level to rise above the opening 7 and the tonometer applanation surface 25.

The latch electromagnet 37 holds the latch ferromagnetic pole piece 35 and the plunger handle 17 down for the duration of the disinfection cycle. During the disinfection cycle the solution level is above the tonometer applanation surface 25 and forms an electrolytic conducting interface between the cell electrodes 31. At the end of the disinfection cycle the latch electromagnet 37 releases the plunger handle 17 allowing the floatation plunger 11 to rise and the solution level to move down to its original level. At this time the tonometer applanation surface 25 and the cell electrodes 31 are no longer immersed in disinfectant solution 3 and the tonometer applanation surface 25 is disinfected and ready for use.

Whenever the fluid level is insufficient, the latch electromagnet 37 and latch ferromagnetic pole piece 35 will not latch and a message to that effect can be made to appear on a display. After a predetermined number of uses or a given period of time, used solution can be removed through the spout 41 and replacement solution poured through the plunger inlet 14.

Figure 6:
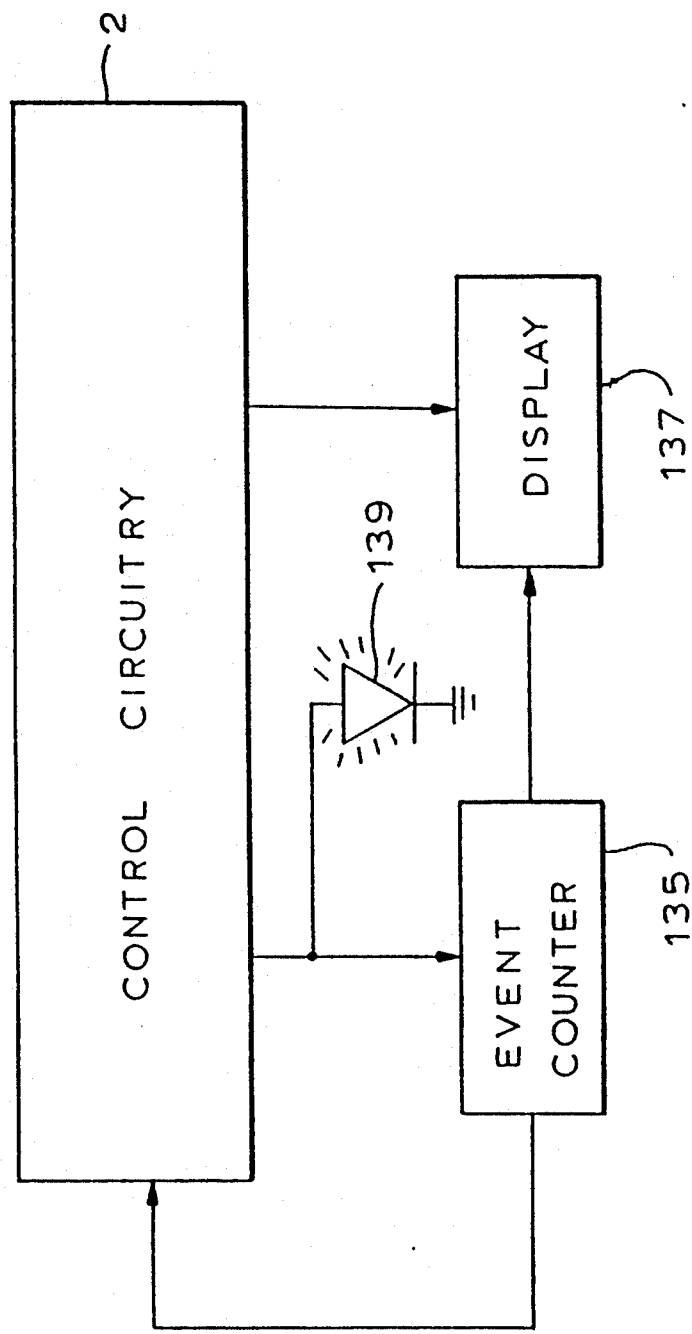
FIG. 6 is a block diagram of the apparatus for monitoring and reporting on the status of the process of the first preferred embodiment of the invention.

Referring now to FIG. 6, there is shown, in block diagram form, an event counter 135 for counting the number of instrument disinfection cycles and a display 137 for displaying appropriate instructive messages. The circuitry employed for counting and display is conventional and will be known to those skilled in the art.

The display 137 presents alphanumeric information regarding system disinfection status. At the termination of the disinfection cycle an indicator, e.g., a green light, which can be an L.E.D. 139, can signal completion of cycle and a ready message can be displayed on the display 137.

Each time a disinfection cycle is completed, a count in the event counter 135 can be incremented. The count can then be compared with a predetermined maximum number of cycles. For example, the above described disinfection fluid should be used only for a limited number of operations, e.g., approximately 30 c.c. for the sooner of for 50 disinfection cycles or an elapsed time of one week. The counter 135 can count the number of cycles. After 50 cycles have been completed, an alphanumeric message can be displayed on the display 137 signaling that the solution should be replaced.

Figure 4:
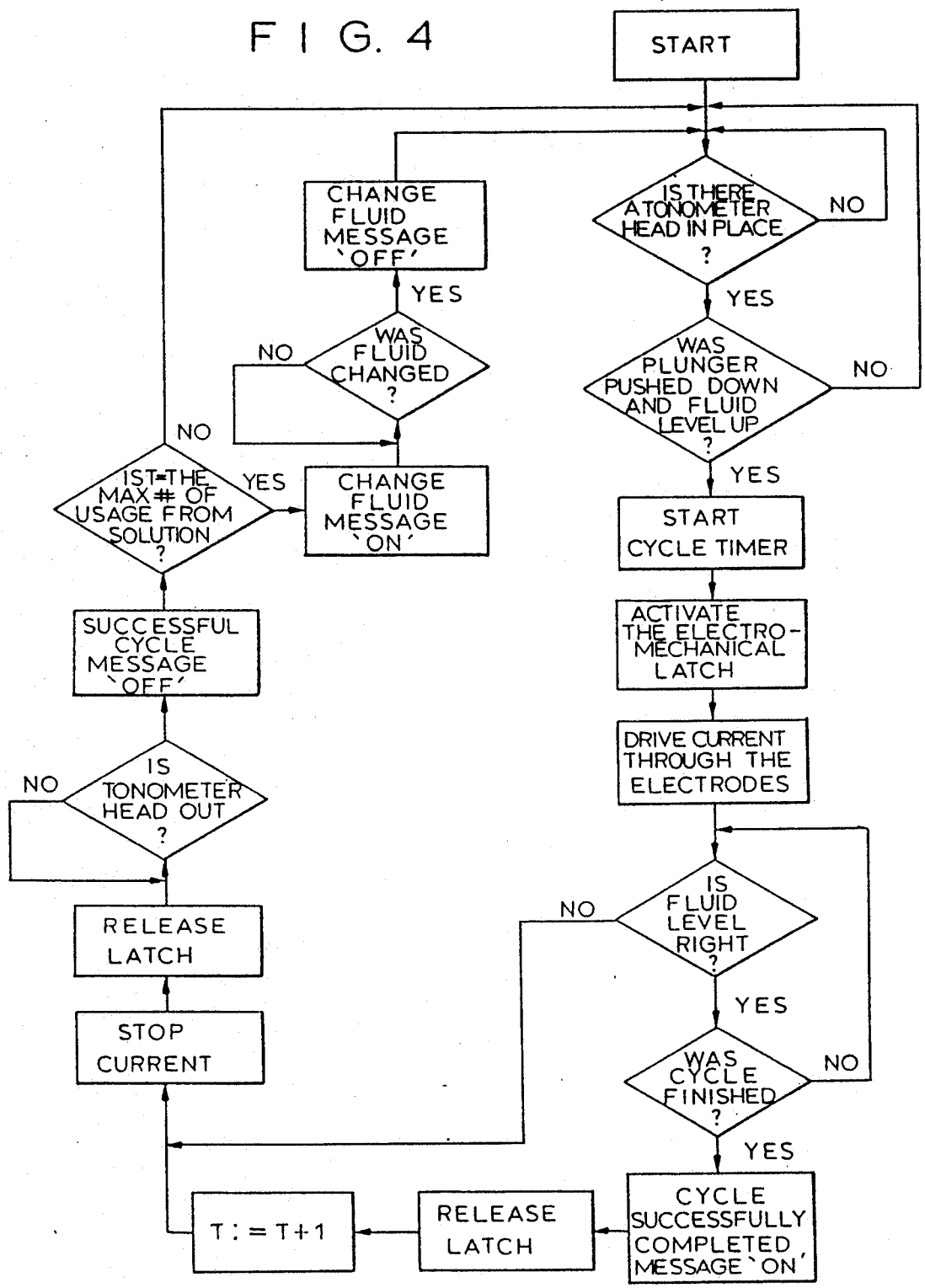
FIG. 4 is a flow diagram illustrating the sequence of operation of the first preferred embodiment of the invention.

Referring to FIG. 4, there is shown a logic flow diagram for the electronics of the apparatus. At power on, the photodiode 27 and photodetector 29 determine whether a tonometer 23 is mounted in the opening 7 of the vessel wall 9 and whether the disinfectant solution 3 is above the electrodes 31 and, hence, the tonometer 23. Only if both conditions prevail does the counter 51 begin its cycle. The latch ferromagnetic pole piece 35 is then latched to the latch electromagnet 37 to hold the plunger handle 17 down.

The system then continuously checks whether the disinfectant solution 3 is above the electrodes 31 and whether the output of the counter 51 indicates an end of the cycle. Successful completion of the cycle can cause an appropriate message to that effect to be displayed, e.g., by lighting an L.E.D. or by displaying a message on an L.E.D. or L.C.D. display. In addition, the latch ferromagnetic pole piece 35 is deenergized to release the floatation plunger 11 and a cycle counter is incremented by one. If the fluid level should drop below the electrodes 31 prior to completion of the cycle governed by the counter 51, no indication of a successful completion is given nor is the cycle counter incremented.

After the tonometer 23 is removed from the vessel 1 and the level of the disinfectant solution 3 drops below the electrodes 31, the successful cycle message is turned off. A determination is then made as to whether the disinfectant solution 3 is due to be changed by comparing the count in the cycle counter with a predetermined stored representation of a number corresponding to the maximum number of permissible cycles for a charge of disinfectant solution 3. Alternatively, a clock may be used to measure elapsed time since the last change of disinfectant solution 3. When the maximum number of cycles is reached or the elapsed time reaches the time for a change of disinfectant solution 3, a change fluid message is displayed. The system is initialized and ready for a new cycle provided that a change of disinfectant solution 3 is done when required. As previously mentioned, the disinfection unit can be mounted on a slit lamp, whereby the tonometer can be easily swung into position, such that the tip is received in the device. Once the tonometer is in the vessel, the handle is pressed to initiate disinfection.

Figure 7:
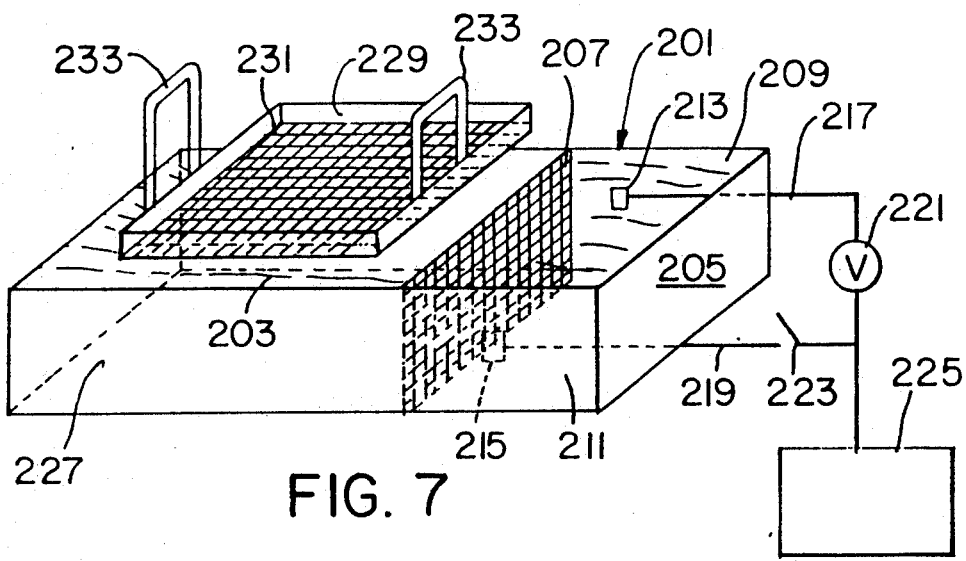
FIG. 7 is a perspective view of a second preferred embodiment of the invention.

Referring now to FIG. 7, there is shown a manually operated system for disinfecting medical instruments, both metallic and non-metallic, e.g., plastic, and other small objects.

An open rectangular tank 201 has two compartments 203 and 205 separated by a mesh wall 207. Mounted on opposite walls 209 and 211 of the compartment 205 are electrodes 213 and 215 which are connected by respective leads 217 and 219 to a voltage source 221. The voltage source 221 may be selectively activated by a switch 223 under the control of a switch controller 225. The switch controller can be in accordance with the control circuitry 2 or any other device for operating a switch either manually or by a timer.

The tank 201 is filled with a buffered salt solution 227 to a level above the electrodes 213 and 215. The solution 227 occupies both compartments 203 and 205 which are in fluid communication through the porous mesh wall 207.

A tray 229 having a porous mesh rectangular bottom 231 is provided with handles 233 extending upwardly from its opposite sides to a height greater than the height of the tank 201. One or more instruments or objects to be disinfected can be placed on the tray bottom 231 and lowered into the tank 201 and submerged in the solution 227 in the compartment 203 where the solution 227 envelops the object(s) or instrument(s).

The foregoing apparatus is particularly well suited for the disinfection of dental instruments. Such instruments generally contain carbon steel which can be oxidized. In order to prevent oxidation, the solution 227 used for such metallic or metallic/plastic instruments has its pH raised to more than 7, preferably between 7 and 10 to prevent oxidation.

The solution 227 includes a stable compound which is not ionized by the system. For example, $Na_3PO_4$ can be used as a stable non-ionizable salt for the system solution 227. The combination of the size of the electrodes 213 and 215 and the magnitude of the voltage applied by the source 221 is adjusted so that the $Na_3PO_4$ does not ionize when the voltage is applied to the solution. An unstable salt which does ionize in response to the same application of voltage and which yields ions that are disinfecting is added to the solution in a quantity which is preferably about ten percent (10%) of the total number of salt moles per liter. $Na_2SO_4$ can be substituted for the $Na_3PO_4$ in the above applications wherein a non-ionizable salt is required.

One salt suitable for providing the disinfecting ions under application of voltage is NaI. The application of voltage causes the NaI to release iodide ions which are a well known powerful disinfectant. Once disassociated from the sodium (Na) ions, during application of voltage, the iodide ions migrate through the solution 227 from the compartment 205 into the compartment 203. There the iodide ions come into contact with infectious organisms carried on the objects or instruments on the tray 201 and destroy them.

The disinfection time is dependent on the concentration of iodide ions, the total surface area of the instruments or objects to be disinfected, and the degree of contamination of the objects or instruments.

Once disinfection is completed, the application of voltage is interrupted by the voltage controller 225. The sodium ions and iodide ions then recombine to form NaI rendering the solution substantially less toxic and safe to discard.

Figure 8:
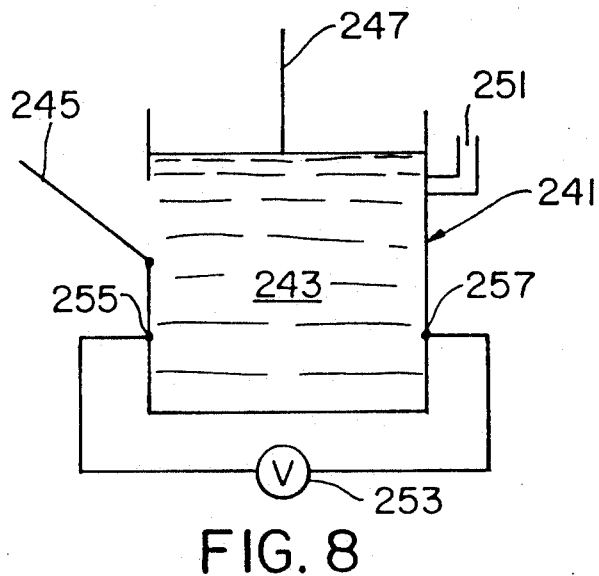
FIG. 8 is a schematic view of a third preferred embodiment of the invention.

Another example of a preferred embodiment of the invention is illustrated in FIG. 8. A compactor has a bin 243 having a chamber in communication with a door 245 which opens to the exterior of the compactor 241. A compression piston 247 which can be operated by an electric motor or a hydraulic or pneumatic mechanism not shown, as will be known those skilled in the art is shown in a raised position. Medical or other infectious waste can be inserted into the compactor 241 through the opening controlled by the door 245. The waste can then be compacted in a manner known in the prior art.

After the waste is compacted, a solution 249 which can be rendered disinfecting by application of voltage is poured into the compactor chamber 243 through a spigot 251 in communication with the chamber 243. The solution 249 can be similar to the solution 227. However, a more active disinfectant is preferable in this application where damage to the mass to be disinfected is not a concern. Instead of NaI, NaF is the preferred ionizable salt constituent of the solution 249. An ionizing voltage is selectively applied to the solution 249 from a source 253 connected to electrodes 255 and 257 mounted on the wall of the compactor bin 243. Fluoride ions are highly toxic to infectious organisms and will decontaminate and disinfect the compacted waste. Thereafter, the waste may be disposed of through channels similar to those generally used for non-hazardous materials.

Figure 9:
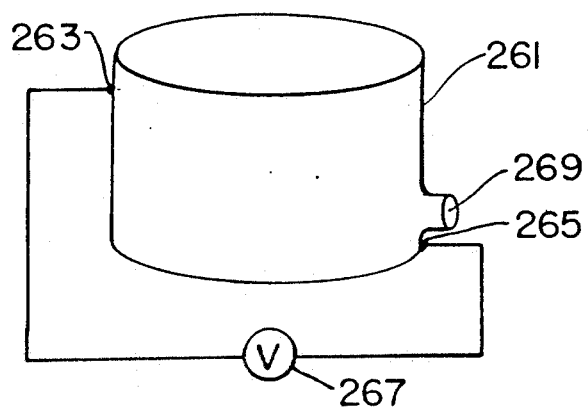
FIG. 9 is a schematic view of a fourth preferred embodiment of the invention.

On a larger scale, the invention may be used for disinfecting waste stored in home or industrial septic tanks. Referring to FIG. 9, there is shown a disinfecting tank 261 which can be fashioned from a conventional 50 gallon steel drum. Electrodes 263 and 265 are mounted on and insulated from the wall of the drum 261. Septic waste is flushed into the drum 261 and then treated with a disinfecting solution which, preferably, includes NaF as the ionizable disinfecting agent. Fluoride ions are generated by application of a voltage from a voltage source 267 connected to the electrodes 263 and 265 for approximately one hour.

After disinfection is completed, the application of voltage is discontinued and the treated waste can be flushed into the septic tank in the ground through an outlet 269. The treated waste will not contaminate underground water supplies.

It is to be appreciated that the foregoing is a description of several preferred embodiments of the invention to which variations and modifications may be made without departing from the spirit and scope of the invention. For example, other objects may be disinfected according to the teachings of the invention such as dishes and other eating and cooking utensils, and even foods such as vegetables and fruits. Electrodes can be provided in a compartment in a dishwasher for ionizing a disinfecting solution in accordance with the invention. In the environment of a dishwasher, the preferred ionizing salt is NaI and the stable salt is $Na_3PO_4$.

In addition, the time periods stated above can be varied. The compartment can be in communication with the main dishwasher chamber for enabling the ionized solution to mix with the circulating water in the dishwasher to disinfect the dishes and other eating utensils being washed. The ionizing voltage is turned off before the end of the dishwasher cycle causing the toxic iodide ions to dissipate.

In order to decontaminate fruits and vegetables in areas where the water is contaminated, or to prolong the shelf life of the fruits and vegetables, the fruits and vegetables can be immersed in a disinfecting solution, in accordance with the invention, containing $Na_3PO_4$ as the stable salt and NaCl as the ionizing salt to generate chloride ions for decontaminating the water and destroying the organisms on the fruits and vegetables. The fruits and vegetables can be placed in a large chamber with the ionization of the disinfecting solution taking place there and the disinfecting solution then being mixed with water in the large chamber for disinfecting the fruits and vegetables. The concentration of the disinfectant solution can be altered in view of the fact that it is being used on ingestible commodities.

What is claimed is:

1. An electrochemical disinfection system for sterilizing an object comprising
   container means for receiving said object while it is being disinfected,
   a solution contained within said container means for enveloping said object while it is received in said container means,
   two electrodes disposed in contact with said solution,
   a voltage source connected between said electrodes for applying a voltage thereacross, and
   a voltage controller for applying said voltage across said electrodes to increase the toxicity of said solution during disinfection and for interrupting application of said voltage to said electrodes to decrease the toxicity of said solution,
   said solution being conductive for conducting an electric current between said electrodes during application of said voltage,
   said current generating ions in said solution for dispersion into contact with said object for disinfecting said object during application of said voltage to said electrodes, said ions recombining upon interruption of said voltage.

2. An electrochemical disinfection system for sterilizing an object according to claim 1 wherein said conductive electrolytic salt is selected from the group consisting of NaCl, $Na_2SO_4$, $Na_3PO_4$, $CaSO_4$, NaI, NaF and KBr.

3. An electrochemical disinfection system for sterilizing an object according to claim 2 further comprising a buffer.

4. An electrochemical disinfection system for sterilizing an object according to claim 3 wherein said buffer is a phosphate buffer.

5. An electrochemical disinfection system for sterilizing an object according to claim 4 wherein said buffer is selected from the group consisting of $NaH_2PO_4$, $Na_2HPO_4$ and $Na_3PO_4$.

6. An electrochemical disinfection system for sterilizing an object according to claim 2 wherein said solution comprises $Na_3PO_4$, NaCl and NaI.

7. An electrochemical disinfection system for sterilizing an object according to claim 6 containing 9.2565 grams per liter of $Na_3PO_4$, 0.88951 grams per liter of NaCl, and 2.295 grams per liter of NaI, each plus or minus 15%.

8. An electrochemical disinfection system for sterilizing an object according to claim 2 wherein said solution comprises $Na_2SO_4$, NaCl and NaI.

9. An electrochemical disinfection system for sterilizing an object according to claim 8 containing 14.484 grams per liter of $Na_2SO_4$, 1.7902 grams per liter of NaCl, and 4.590 grams per liter of NaI, each plus or minus 15%.

10. A method of disinfecting an object comprising electrolyzing a solution of a stable salt and an unstable salt by a applying a voltage across it to cause the unstable salt to release toxic ions, dispersing said toxic ions in said solution about the object until it is disinfected, and, thereafter, interrupting said voltage to render said solution non-toxic.

11. A method of disinfecting an object according to claim 10 further comprising adding a base to said solution to raise its pH to between 5 and 8 for disinfecting metallic and/or plastic instruments without oxidation.

12. A method of disinfecting fruits and/or vegetables comprising immersing the fruits or vegetables in a solution comprising a stable salt and an unstable salt, and applying a voltage across that solution to render the solution disinfecting for decontaminating or preserving the shelf life of said fruits and/or vegetables.

* * * * *